United States Patent
Baumann et al.

(10) Patent No.: US 7,653,177 B2
(45) Date of Patent: Jan. 26, 2010

(54) MEASUREMENT SYSTEM AND METHOD FOR THE NONINVASIVE DETERMINATION OF PROPERTIES OF AN OBJECT TO BE EXAMINED AND CONTRAST MEDIUM X-RAY PHASE-CONTRAST MEASUREMENT

(75) Inventors: Joachim Baumann, Munich (DE); Christian David, Lauchringen (DE); Martin Engelhardt, Munich (DE); Jörg Freudenberger, Kalchreuth (DE); Eckhard Hempel, Fürth (DE); Martin Hoheisel, Erlangen (DE); Matthias Honal, Munich (DE); Thomas Mertelmeier, Erlangen (DE); Franz Pfeiffer, Brugg (CH); Stefan Popescu, Erlangen (DE); Manfred Schuster, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/213,945

(22) Filed: Jun. 26, 2008

(65) Prior Publication Data
US 2009/0003526 A1    Jan. 1, 2009

(30) Foreign Application Priority Data
Jun. 27, 2007   (DE) .................. 10 2007 029 730

(51) Int. Cl.
*G01N 23/20* (2006.01)
(52) U.S. Cl. .......................................... 378/70; 378/71
(58) Field of Classification Search .................... 378/4, 378/5, 62–65, 71–74
See application file for complete search history.

(56) References Cited

U.S. PATENT DOCUMENTS

| 4,938,901 | A | 7/1990 | Groitzsch |
| 7,351,221 | B2* | 4/2008 | Trombley et al. ............. 604/82 |
| 2002/0165445 | A1* | 11/2002 | Uber et al. .................. 600/407 |
| 2005/0286680 | A1 | 12/2005 | Momose |
| 2006/0235296 | A1 | 10/2006 | Mattiuzzi et al. |
| 2007/0183560 | A1 | 8/2007 | Popescu et al. |
| 2007/0183562 | A1 | 8/2007 | Popescu et al. |
| 2007/0183580 | A1 | 8/2007 | Popescu et al. |

(Continued)

FOREIGN PATENT DOCUMENTS

DE    102006015355    8/2007

(Continued)

OTHER PUBLICATIONS

Momose, A. (u.a.), "Blood Vessels: Depiction at Phase-Contrast X-ray Imaging without Contrast Agents in the Mouse and Rat-Feasibility Study", Radiology, 2000, S. 593-596; Others; 2000.

(Continued)

*Primary Examiner*—Irakli Kiknadze
(74) *Attorney, Agent, or Firm*—Harness, Dickey & Pierce, P.L.C.

(57) ABSTRACT

A method and a measurement system are disclosed for the noninvasive determination of properties of an object to be examined and to the use of a contrast medium for X-ray phase-contrast measurement. in at least one embodiment of the invention, a mixture (suspension) consisting of a base liquid and a multiplicity of particles contained therein is used, the refractive index of the base liquid being different to the refractive index of the particles.

22 Claims, 4 Drawing Sheets

U.S. PATENT DOCUMENTS

2007/0183581 A1    8/2007    Heismann et al.

FOREIGN PATENT DOCUMENTS

| | | |
|---|---|---|
| DE | 102006015355 A1 | 8/2007 |
| DE | 102006015356    | 8/2007 |
| DE | 102006015356 A1 | 8/2007 |
| DE | 102006015358    | 8/2007 |
| DE | 102006015358 A1 | 8/2007 |
| DE | 102006017290    | 8/2007 |
| DE | 102006017290 A1 | 8/2007 |
| DE | 102006017291    | 8/2007 |
| DE | 102006017291 A1 | 8/2007 |
| EP | 1 447 046       | 8/2004 |
| EP | 1447046 A1      | 8/2004 |
| EP | 1731099 A1      | 12/2006 |
| EP | 1810698 A1      | 7/2007 |
| WO | WO 2004071535 A1 | 8/2004 |

OTHER PUBLICATIONS

Born, M., Wolf, E: "Principles of optis". Cambridge: Cambridge University Press, 7. Auflage, 1999, ISBN 0 521 642221, S. 16-17; Others; 1999.

German Patent Office Action dated Sep. 25, 2007.

\* cited by examiner

MEASUREMENT SYSTEM AND METHOD FOR THE NONINVASIVE DETERMINATION OF PROPERTIES OF AN OBJECT TO BE EXAMINED AND CONTRAST MEDIUM X-RAY PHASE-CONTRAST MEASUREMENT

PRIORITY STATEMENT

The present application hereby claims priority under 35 U.S.C. §119 on German patent application number DE 10 2007 029 730.2 filed Jun. 27, 2007, the entire contents of which is hereby incorporated herein by reference.

FIELD

Embodiments of the invention generally relate to a measurement system for the noninvasive determination of properties of an object to be examined and/or processes and/or states in an object to be examined by determining the relative phase shift of at least two neighboring coherent X-ray beams which pass through the object to be examined on a defined path.

Embodiments of the invention furthermore generally relate to a contrast medium for use in an X-ray contrast measurement, including the use of this contrast medium.

Furthermore, embodiments of the invention also generally relate to a method for the noninvasive determination of properties of an object to be examined and/or processes and/or states in an object to be examined by determining the relative phase shift of at least two neighboring coherent X-ray beams which pass through the object to be examined on a defined path.

BACKGROUND

Measurement systems and methods for the noninvasive determination of properties of an object to be examined and/or processes and/or states in an object to be examined by determining the relative phase shift are fundamentally known. For example, reference may be made to European patent application EP 1 447 046 A1 and the German patent applications by the Applicant with the application numbers 10 2006 017 290.6, 10 2006 015 358.8, 10 2006 017 291.4, 10 2006 015 356.1 and 10 2006 015 355.3.

In the field of computer tomography, it is widely known to use phase-contrast media with greatly increased X-ray absorption values in order to be able to better differentiate the contrast between regions with and without incorporated contrast medium.

To improve the image representation, it is thus desirable on the one hand to find media which increase as much as possible the phase shift of the X-radiation passing through the object to be examined in selected regions, in order to achieve a maximally high contrast. Owing to the nature of phase-contrast measurement, at least with non-integrative scanning, phase differences of more than $\pi/2$ lead again to lower contrast. Phase shifts which are multiples of $\pi/2$ also cannot lead to higher contrasts. Depending on the measurement conditions, this may sometimes entail a reduction of the integratively measured phase shift being induced with the aid of the contrast medium, in order to obtain a phase shift in the increasing range of from 0 to $\pi/2$ at the detector.

SUMMARY

In at least one embodiment of the invention, a measurement system and a method are disclosed for the noninvasive determination of properties of an object to be examined and/or processes and/or states in an object to be examined by determining the relative phase shift, so that structures in the object to be examined can be identified better, i.e. the relative phase shifts as far as possible vary in the range of from 0 to $\pi/2$.

Accordingly, in at least one embodiment, the Inventors therefore provide a measurement system for the noninvasive determination of properties of an object to be examined and/or processes and/or states in an object to be examined by determining the relative phase shift of at least two neighboring coherent X-ray beams which pass through the object to be examined on a defined path, comprising:

an X-ray source which indirectly or directly generates the at least two mutually coherent X-ray beams with a wavelength $\lambda$, a detector system which is arranged at a distance $z_1$ from the object to be examined and is suitable for determining the relative phase shift $\Phi$ of the at least two X-ray beams, and a phase-contrast contrast medium (suspension) consisting of a base liquid and a multiplicity of particles contained therein, the refractive index $n_B$ of the base liquid being different to the refractive index $n_P$ of the particles.

The measurement system defined above may also be configured so that in accordance with a space to be observed in the object to be examined, which has an internal width L in the propagation direction of the measurement beams, an average radius r which satisfies the geometrical relation $$r \gg \sqrt[4]{2\lambda z_1 L^2}$$

is selected for the particles in the phase-contrast contrast medium. With respect to the term "average radius", it should be pointed out that for particles of general shape, this is intended to mean the radius of a sphere which circumscribes the particle and whose radius r reflects the most frequently occurring penetration lengths of the radiation.

The particle size is preferably selected according to the geometrical proportions of the space to be observed, so that the following geometrical relation is satisfied $$2r = \kappa \frac{\lambda}{\delta_P - \delta_B},$$

where $\kappa$ can take a value range of from 1% to 99%, and $\delta_P$ and $\delta_B$, respectively correspond to the real decrements of the refractive indices $n_P$ and $n_B$.

In an example refinement, the measurement system may in particular use particles in the contrast medium which are designed convexly, in particular as solid spheres or cylinders or as polyhedra. The particles may in this case have an outer cladding and a core, respectively with different refractive indices.

The measurement system may furthermore be configured so that the X-ray source and the detector are arranged statically relative to the object to be examined. With such an arrangement, the object to be examined itself is moved relative to the radiation source and the detector. As an alternative, the X-ray source and the detector may also be designed rotatably relative to the object to be examined, so that the X-ray source and the detector rotate around the object to be examined according to a medical CT known per se.

The measurement system may furthermore comprise a detector which is designed flatly and includes a multiplicity of individual detector elements.

According to the basic inventive concepts, in at least one embodiment the Inventors also disclose a contrast medium for use in an X-ray contrast measurement, wherein it consists of a base liquid and a multiplicity of particles contained therein, the refractive index $n_B$ of the base liquid being different to the refractive index $n_P$ of the particles.

In this contrast medium, a particle size is preferably provided which satisfies the following geometrical relation $$2r = \kappa \frac{\lambda}{\delta_P - \delta_B},$$

where r is the parameter radius, κ can take a value range of from 1% to 99%, and $\delta_P$ and $\delta_B$ respectively correspond to the real decrements of the refractive indices np and $n_B$ and λ represents the wavelength of the X-radiation being used.

Also disclosed is a use of a contrast medium for X-ray phase-contrast measurement, consisting of a base liquid and a multiplicity of particles contained therein, the refractive index $n_B$ of the base liquid being different to the refractive index $n_P$ of the particles.

For this use of the contrast medium laden with particles, it is also proposed that a particle size should be used which satisfies the following geometrical relation $$2r = \kappa \frac{\lambda}{\delta_P - \delta_B},$$

where r is the parameter radius, κ can take a value range of from 1% to 99%, and $\delta_P$ and $\delta_B$ respectively correspond to the real decrements of the refractive indices $n_P$ and $n_B$ and λ represents the wavelength of the X-radiation being used.

The object to be examined may furthermore comprise a space to be observed, which has an internal width L in the direction of the measurement beams so that the following geometrical relation $$r \gg \sqrt[4]{2\lambda z_1 L^2}$$

is satisfied.

The particles used may preferably be convexly designed, shapes corresponding to a solid sphere or an ellipsoid or a cylinder or a polyhedron being preferred. When using such particles, they may preferably also have an outer cladding and a core, respectively with different refractive indices.

At least one embodiment of the invention also provides a method for the noninvasive determination of properties of an object to be examined and/or processes and/or states in an object to be examined by determining the relative phase shift of at least two neighboring coherent X-ray beams which pass through the object to be examined on a defined path, wherein:

a contrast medium consisting of a suspension, with a base liquid and a multiplicity of particles contained therein, is applied into the object to be examined, the refractive index $n_B$ of the base liquid being different to the refractive index $n_P$ of the particles, at least two mutually coherent X-ray beams with a wavelength λ are generated with the aid of an X-ray source and propagate through the object to be examined, including the applied contrast medium, and the relative phase shift Φ of the at least two X-ray beams when they pass through the object to be examined and through the particles in the contrast medium is determined by a detector system which is arranged at a distance z from the object to be examined.

BRIEF DESCRIPTION OF THE DRAWINGS

Embodiments of the invention will be described in more detail below with the aid of the figures, only the features necessary for understanding the invention being represented.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Depending on specific applications, for example the medical diagnosis of blood vessels, the digestive tract or respiratory organs, image representations of marks in medical, pharmaceutical and biological examinations, nondestructive examinations of thin gaps, narrow holes or pores in workpieces or the imaging of intermixed powders, liquids or gases and the like, different special embodiments of the measurement system are necessary. Irrespective of this, however, the basic inventive idea relating to the contrast medium for the phase-contrast examination will be described as follows:

In contrast medium examinations, a material that fills a contour which is intended to be represented is replaced by another material, which has a significantly higher or lower mass density. According to the formula $$\delta = \frac{r_0 N_A \rho Z \lambda^2}{2\pi A_r} \quad [1]$$

for the real decrement $\delta$, changing the material leads to a change of the refractive index and causes a variation in the phase shift. In this Equation (1): $r_0$ denotes the classical electron radius, $N_A$ denotes Avogadro's number, Z denotes the atomic number, $A_r$ denotes the relative atomic mass and $\rho$ denotes the mass density. When the phase shift change is more than 1% of $\pi$, this variation can be measured and represented as an image by a known measurement method of phase-contrast imaging. This also applies to phase-contrast measurements which allow quantitative determination of the phase in each pixel.

Homogeneous materials with different mass densities, which replace an existing material in a given contour, may for example be used as a contrast medium. In this case, the phase-contrast effect is based exclusively on the difference in the mass density $\rho$ and the real decrement $\delta$ according to the equations mentioned above.

Phase contrast may, however, also be based on shapes and sizes in which the contrast medium is present. The contrast medium may for example be present in a dispersion-like consistency, for example as slurry or liquid suspension with small spheres of well-defined shape and size distributed therein.

Figure 1:
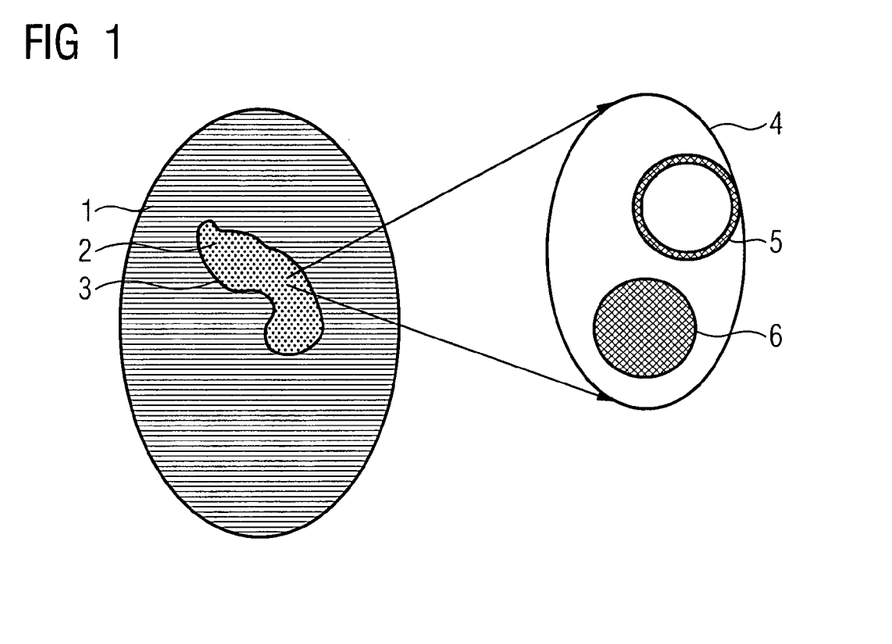
FIG. 1: shows a representation of an object to be examined with an opening filled with phase-contrast contrast medium.

FIG. 1 shows a contrast medium 2 filled with small spheres 5 and 6, which fills an opening 3 in an object to be examined or organ 1. Such spheres may for example be designed as hollow spheres 5, i.e. as spheres with a thin wall and a sphere interior which consists of a different material to the wall. This interior may for example consist of gas, liquid or solids. On the other hand, the spheres may also be designed as solid spheres 6 made of a single material as shown in detail 4.

Variations in the interaction thickness or the real decrement in the object or the contrast medium affects the wavefront. The phase shift $\Phi$ of a ray on its path through an object relative to a vacuum is given by $$\Phi(x, y) = -\frac{2\pi}{\lambda} \int_{-\infty}^{+\infty} \delta(x, y, z) dz. \quad [2]$$

Figure 2:
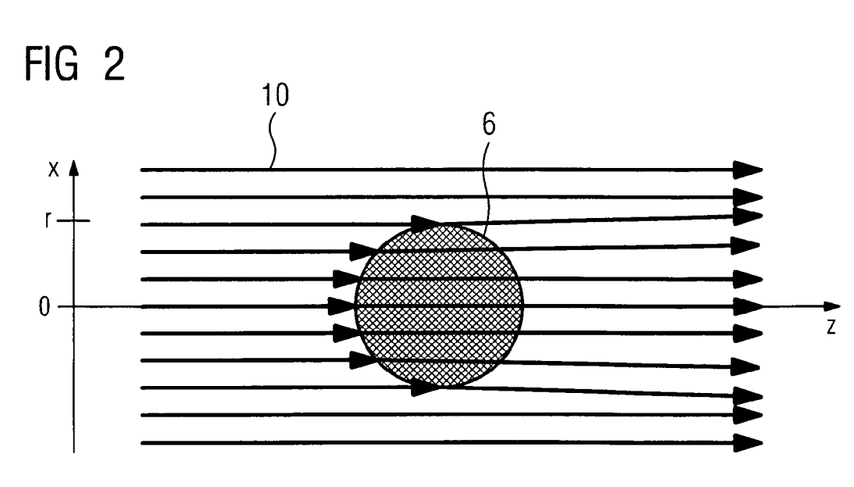
FIG. 2: shows a schematic representation of X-rays when they pass through a particle of the contrast medium according to an embodiment of the invention.

For the sake of simplicity, it may be assumed that the object is a homogeneous sphere with a radius r and a real decrement $\delta_0$. Restriction to a two-dimensional geometry may also be adopted, x representing the transverse direction and z representing the propagation direction of the radiation 10—symbolized by the arrows pointing from left to right—as shown in FIG. 2.

This simplification gives the following equation for the phase shift $\Phi$ of a ray on its path through the sphere 6 shown $$\Phi(x) = -\frac{2\pi}{\lambda} \int_{-\sqrt{r^2-x^2}}^{+\sqrt{r^2-x^2}} \delta_0 \, dz = -\frac{2\pi}{\lambda} 2\delta_0 \sqrt{r^2 - x^2}. \quad [3]$$

Figure 3:
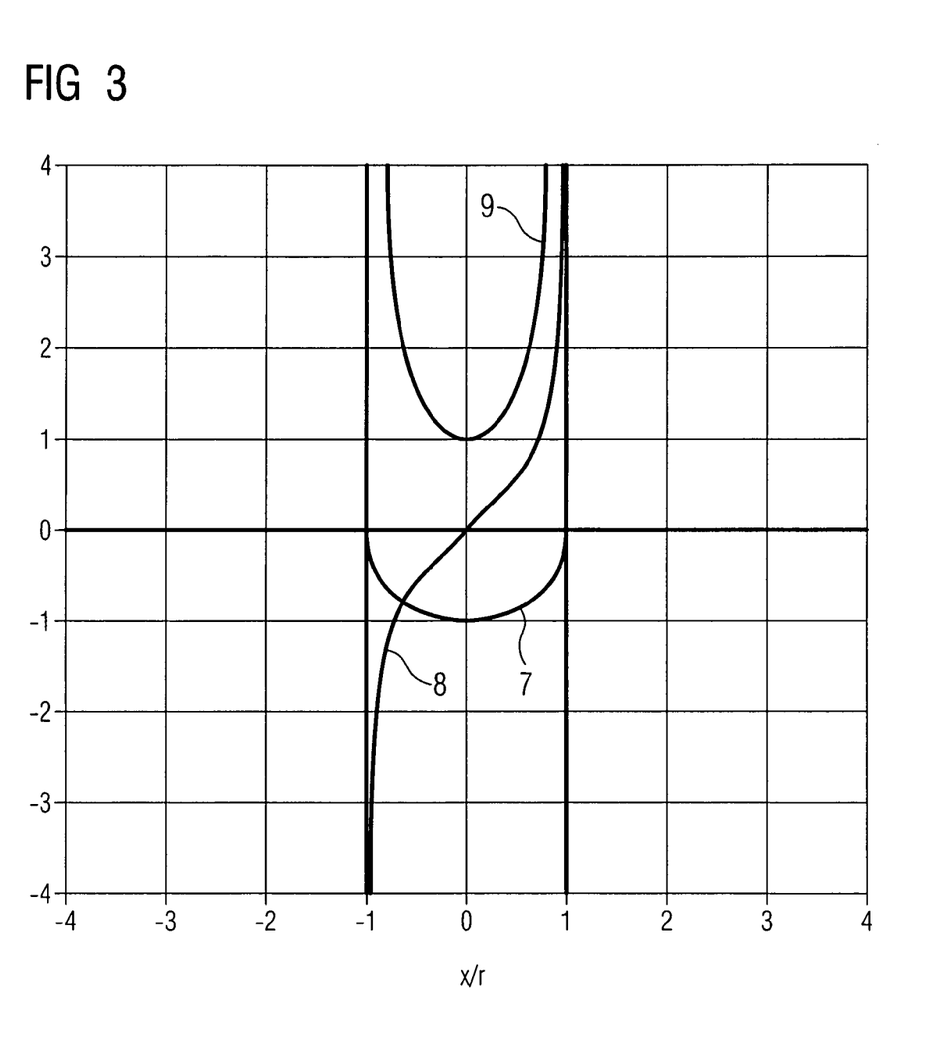
FIG. 3: shows a functional profile of the zeroth, first and second spatial derivatives of the phase shift Φ (x)

The profile of this function $\Phi(x)$ is represented in FIG. 3 by the reference numeral 7. The gradient of the phase shift determines the direction of the wave propagation. In the axially parallel case, the angular deviation $\Delta\theta$ of the incident wavefront is approximated by the equation $$\Delta\theta(x) = \frac{\lambda}{2n}\frac{\partial}{\partial x}\Phi(x) = 2\delta_0 \frac{x}{\sqrt{r^2 x^2}}. \quad [4]$$

The functional relationship of $\Delta\theta$ is represented in FIG. 3 by the reference numeral 8. For the Fresnel propagation case, by using Kirchhoff's integral, the intensity in the imaging at $z_1$ can be approximated by the equation $$I(x) = I_0 \left(\frac{z_0}{z_0 + z_1}\right)^2 \left[1 + \frac{2\pi}{\lambda} \frac{z_0 z_1}{z_0 + z_1} \frac{\partial^2}{\partial x^2}\Phi(x)\right] \quad [5]$$

and the following is obtained for a homogeneous sphere:

$$I(x) = I_0 \left(\frac{z_0}{z_0 + z_1}\right)^2 \left[1 + \frac{2\pi}{\lambda} \frac{z_0 z_1}{z_0 + z_1} 2\delta_0 \frac{r^2}{(r^2 - x^2)^{3/2}}\right] \quad [6]$$

This functional behavior is shown in FIG. 3 by the reference numeral 9. According to Equation 6, the intensity diverges at the edge of the sphere or cylinder, i.e. for $x \to r$.

Figure 4:
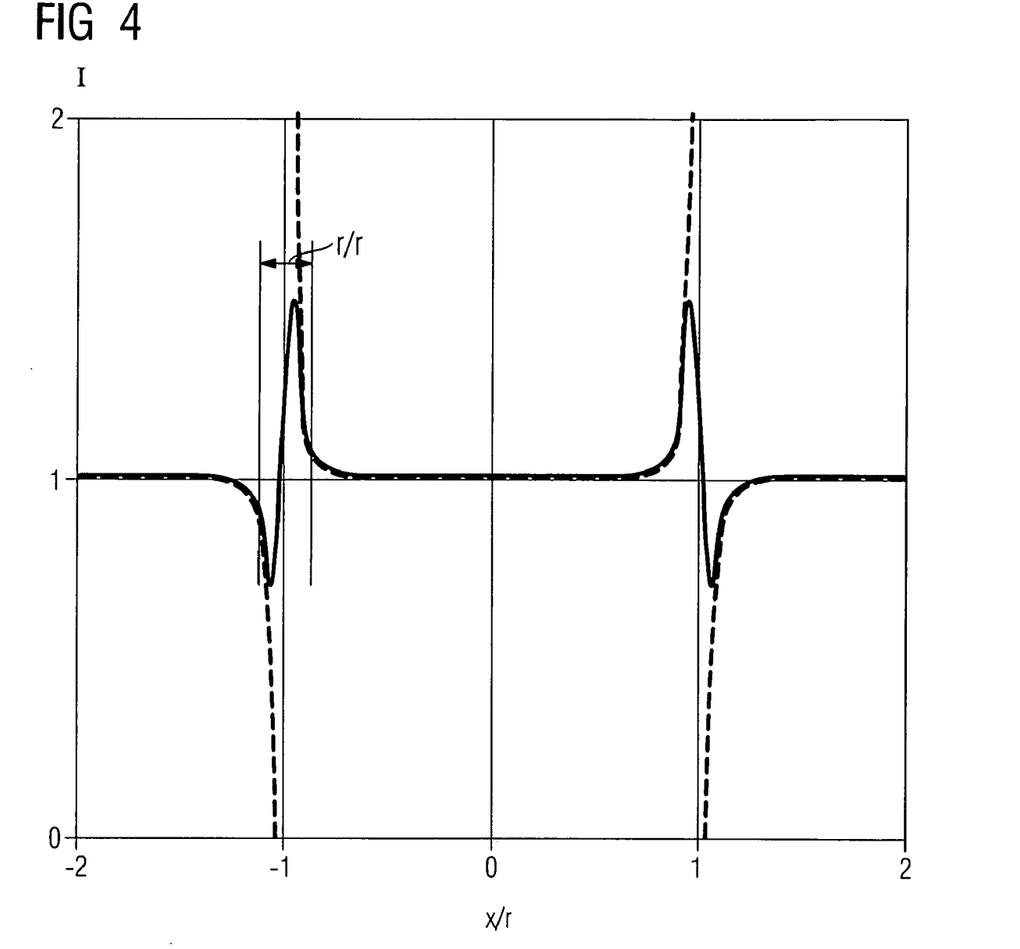
FIG. 4: shows an intensity profile relative to a transverse coordinate of a phase-contrast image of a sphere with radius r.

Although these considerations apply only approximately, they nevertheless make it possible to study the trend in respect of object sizes and shapes, X-ray optical material properties and the geometry of the beam path. Besides the amplitude, the intensity oscillation, which is observed in more accurate simulations and experiments, also shows a significant broadness. While the amplitude of the oscillation is strongly influenced by the coherence length at the observation point, the width of the oscillation does not vary significantly. The broadness of the oscillation can be described by the energy spectrum of the spatial frequency, and a functional relationship as represented in FIG. 4 is obtained.

The dominant spatial frequency f correlates with the oscillation and is given by the equation:

$$f = \sqrt{\frac{1}{2\lambda z_1}}. \quad [7]$$

The width of the oscillation can be approximated by the equation:

$$\Delta r = \frac{1}{f}. \quad [8]$$

Hollow spheres are imaged as a black/white contrast ring at the edges. This is a general property of phase-contrast imaging which is not restricted to mathematical spheres; rather, it can be seen at all object edges. This property is due to the Laplace operator of the distribution of the refractive index, which is to be found in the second term of Equation [5].

Figure 5:
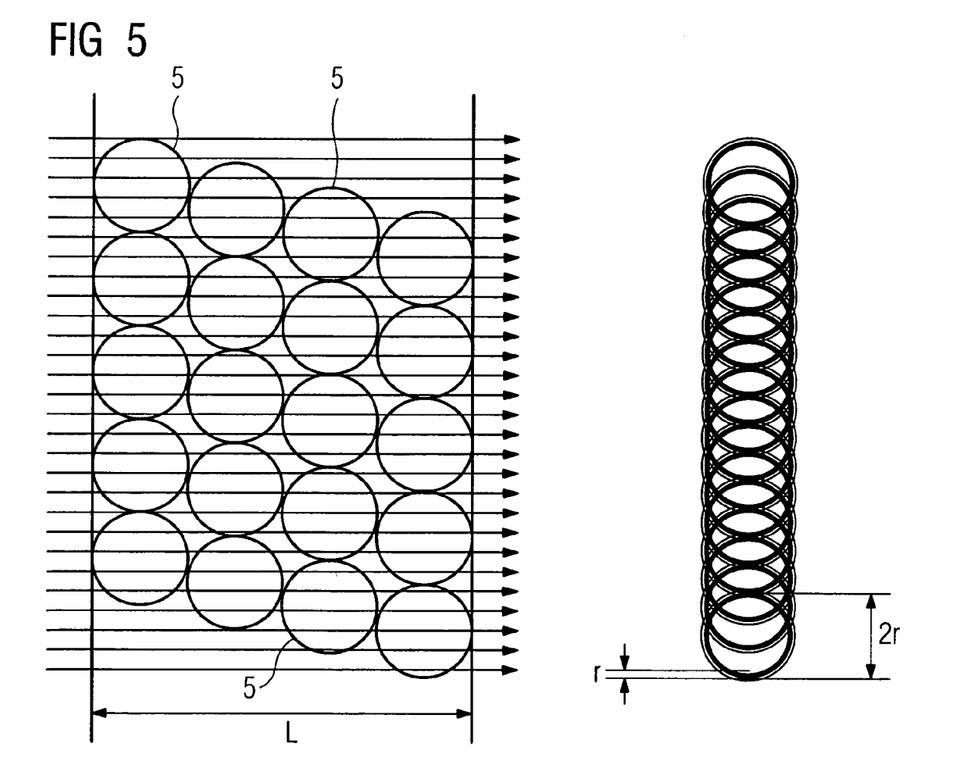
FIG. 5: shows a schematic representation of a phase-contrast contrast medium according to an embodiment of the invention with small spheres of radius r in an opening of size L.

The use of hollow spheres or spheres as a contrast medium lead to clearly visible edges in the phase-contrast image in the form of black/white rings, as is shown for example in FIG. 5 for the example of hollow spheres, which can be detected with the aid of standard methods in image processing. This applies so long as these black/white rings can clearly be seen separately from one another.

In practical use, the contrast medium may for example be a dispersion with a multiplicity of small spheres, which are arranged in an opening or in an organ in order to be represented as an image. In such applications, many hollow spheres may be positioned successively along the optical path. So that such individual spheres can be observed individually in respect of their edges, the radii of the spheres or the radii of the particles being used must satisfy the following conditions:

$$r^2 >> L\sqrt{2\lambda z_1} \quad [9],$$

where L describes the length of the radiation path through an opening or an organ. This condition can be rewritten as:

$$r >> (2\lambda z_1 L^2)^{1/4} \quad [10],$$

Thus if for example the size L of the opening is one centimeter, a wavelength of $\lambda=0.05$ nm corresponding to a photon energy of 24.8 keV and the distance between the image or detector is $z_1=0.2$ m, then the radius r of the spheres must be large compared with 200 µm. This example illustrates that in practice many applications are made possible by varying the wavelength, the object-image distance and the sphere radius. The condition of Equation [10] gives a lower limit for the radius of the spheres or particle sizes being used.

On the other hand, the expression for the intensity oscillation or intensity modulation of Equations [5] or [6] shows that the contrast i.e. the oscillation amplitude increases as the radius becomes smaller. For each application, the optimal condition with respect to the radius r of the spheres being used should thus be selected so that it lies within the constraint of Equations [5], [6] and [10]. Equation [10] applies for ideal cases of sharp transitions between the spheres of the contrast medium and the surrounding material, i.e. with discontinuous changes in the refractive index. A softer transition of the refractive index may increase the broadness $\Delta r$ of the oscillation. The same applies with respect to the roughness of the surface of the contrast medium spheres. The coherence length is affected less according to an initial consideration, but it influences the oscillation amplitude so that a reduction of the coherence length likewise reduces the oscillation amplitude and stringent requirements are entailed with respect to the coherence length. Typical coherence lengths are more than 1 µm.

The conditions for the phase-contrast contrast medium described in the introduction, in particular for the particles contained therein, are obtained according to these considerations as described above.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A measurement system for the noninvasive determination of at least one of properties of an object to be examined, processes in an object to be examined and states in an object to be examined by determining the relative phase shift of at least two neighboring coherent X-ray beams which pass through the object to be examined on a defined path, the system comprising:
    an X-ray source which indirectly or directly generates the at least two mutually coherent X-ray beams with a wavelength $\lambda$;
    a detector system, arranged at a distance $z_1$ from the object to be examined and suitable for determining the relative phase shift $\Phi$ of the at least two X-ray beams; and
    a phase-contrast contrast medium consisting of a base liquid and a multiplicity of particles contained therein, the refractive index $n_B$ of the base liquid being different to the refractive index $n_P$ of the particles.

2. The measurement system as claimed in claim 1, wherein the object to be examined includes a space to be observed, which has an internal width L in the propagation direction of the measurement beams, and an average radius r which satisfies the geometrical relation $$r \gg \sqrt[4]{2\lambda z_1 L^2}$$

is selected for the particles in the phase-contrast contrast medium.

3. The measurement system as claimed in claim 2, wherein an average particle radius r is selected which satisfies the following geometrical relation:

$$2r = \kappa \frac{\lambda}{\delta_P - \delta_B},$$

where $\kappa$ can take a value range of from 1% to 99%, and $\delta_P$ and $\delta_B$ respectively correspond to the real decrements of the refractive indices $n_P$ and $n_B$.

4. The measurement system as claimed in claim 1, wherein an average particle radius r is selected which satisfies the following geometrical relation:

$$2r = \kappa \frac{\lambda}{\delta_P - \delta_B},$$

where k is a value range of from 1% to 99%, and $\delta_P$ and $\delta_B$ respectively correspond to the real decrements of the refractive indices $n_P$ and $n_B$.

5. The measurement system as claimed in claim 1, wherein the particles are convexly designed.

6. The measurement system as claimed in claim 1, wherein the particles are designed as solid spheres.

7. The measurement system as claimed in claim 1, wherein the particles are designed as cylinders.

8. The measurement system as claimed in claim 1, wherein the particles are designed as polyhedra.

9. The measurement system as claimed in claim 1, wherein the particles have an outer cladding and a core, respectively with different refractive indices.

10. The measurement system as claimed in claim 1, wherein the X-ray source and the detector are arranged statically relative to the object to be examined.

11. The measurement system as claimed in claim 1, wherein the X-ray source and the detector are arranged rotatably relative to the object to be examined.

12. The measurement system as claimed in claim 1, wherein the detector is designed flatly and includes a multiplicity of individual detector elements.

13. A contrast medium for use in an X-ray contrast measurement, comprising:
    a base liquid and a multiplicity of particles contained therein, the refractive index $n_B$ of the base liquid being different to the refractive Index $n_P$ of the particles, wherein
    a particle size is provided which satisfies the following geometrical relation $$2r = \kappa \frac{\lambda}{\delta_P - \delta_B},$$

where r is the parameter radius, k is a value range of from 1% to 99%, and $\delta_P$ and $\delta_B$ respectively correspond to the real decrements of the refractive indices $n_P$ and $n_B$ and $\lambda$ represents the wavelength of the X-radiation being used.

14. A method, comprising:
    using a contrast medium for X-ray phase-contrast measurement, the contrast medium consisting of a base liquid and a multiplicity of particles contained therein, the refractive index $n_B$ of the base liquid being different to the refractive index $n_P$ of the particles, wherein
    a particle size is used which satisfies the following geometrical relation $$2r = \kappa \frac{\lambda}{\delta_P - \delta_B},$$

where r is the parameter radius, k is a value range of from 1% to 99%, and $\delta_P$ and $\delta_B$ respectively correspond to the real decrements of the refractive indices $n_P$ and $n_B$ and $\lambda$ represents the wavelength of the X-radiation being used.

15. The method according to claim 14, wherein the object to be examined includes a space to be observed, which has an internal width L in the direction of the measurement beams, and particles with an average radius r which satisfies the geometrical relation $$r \gg \sqrt[4]{2\lambda z_1 L^2}$$

are used in the particles in the phase-contrast contrast medium.

16. The method according to claim 14, wherein the particles are convexly designed.

17. The method according to claim 14, wherein the particles are designed as solid spheres.

18. The method according to claim 14, wherein the particles are designed as cylinders.

19. The method according to claim 14, wherein the particles are designed as polyhedra.

20. The method according to claim 14, wherein the particles have an outer cladding and a core, respectively with different refractive indices.

21. The method according to claim 14, wherein the object to be examined includes a space to be observed, which has an internal width L in the direction of the measurement beams, and particles with an average radius r which satisfies the geometrical relation $$r \gg \sqrt[4]{2\lambda z_1 L^2}$$

are used in the particles in the phase-contrast contrast medium.

22. A method for the noninvasive determination of at least one of properties of an object to be examined, processes in an object to be examined and states in an object to be examined by determining the relative phase shift of at least two neighboring coherent X-ray beams which pass through the object to be examined on a defined path, the method comprising:
  applying a contrast medium, consisting of a suspension with a base liquid and a multiplicity of particles contained therein, into the object to be examined, the refractive index of the base liquid being different to the refractive index of the particles;
  generating at least two mutually coherent X-ray beams with a wavelength with the aid of an X-ray source and propagating them through the object to be examined, including the applied contrast medium; and
  determining a relative phase shift of the at least two X-ray beams, when they pass through the object to be examined and through the particles in the contrast medium, using a detector system, arranged at a distance from the object to be examined.

* * * * *